United States Patent [19]

Wolter et al.

[11] 4,203,253

[45] May 20, 1980

[54] PROCESS FOR INCREASING OLEORESIN SYNTHESIS IN PINUS SPECIES

[75] Inventors: Karl E. Wolter, Evansville, Wis.; William J. Peters, Lake City, Fla.; Donald R. Roberts, Gainesville, Fla.; Robert D. McReynolds, Lake City, Fla.; Junior Broomfield; Ernest R. Crews, both of Olustee, Fla.

[73] Assignee: The United States of America as represented by the Secretary of Agriculture, Washington, D.C.

[21] Appl. No.: 3,700

[22] Filed: Jan. 16, 1979

Related U.S. Application Data

[63] Continuation-in-part of Ser. No. 869,891, Jan. 16, 1978, abandoned.

[51] Int. Cl.² .............. A01G 23/10; A01N 5/00; A01N 9/36
[52] U.S. Cl. ................................. 47/10; 71/86
[58] Field of Search .......................... 71/86; 47/10

[56] References Cited

U.S. PATENT DOCUMENTS

| | | | |
|---|---|---|---|
| 3,839,823 | 10/1974 | Roberts et al. | 47/10 |
| 3,879,188 | 4/1975 | Fritz et al. | 71/86 |
| 3,991,515 | 11/1976 | Drew | 47/10 |

FOREIGN PATENT DOCUMENTS

| | | | |
|---|---|---|---|
| 1293934 | 10/1972 | United Kingdom | 47/10 |
| 1438416 | 6/1976 | United Kingdom | 47/10 |

Primary Examiner—Robert E. Bagwill
Attorney, Agent, or Firm—M. Howard Silverstein; David G. McConnell

[57] ABSTRACT

Stimulation of oleoresin production associated with living cells can be chemically induced with dilute systemic application of ethylene or ethylene-releasing compounds. One such ethylene-releasing compound is 2-chloroethylphosphonic acid. A further increase in oleoresin production can be accomplished by using ethylene-releasing chemicals in combination with the bipyridilium salts, diquat or paraquat. Through the application of ethylene-releasing chemicals in combination with a bipyridilium salt, the effect of lightwood inducing chemicals is expanded over a larger portion of the treated tree, and more oleoresin is produced. Oleoresins are extracted from the trees by known methods, and the naval stores products are recovered therefrom.

5 Claims, No Drawings

PROCESS FOR INCREASING OLEORESIN SYNTHESIS IN PINUS SPECIES

This is a continuation-in-part application of our pending Ser. No. 869,891, filed on Jan. 16, 1978 (now abandoned).

BACKGROUND OF THE INVENTION

1. Field of the Invention:

This invention relates to an improvement (specifically, significantly less toxic) for chemically inducing the stimulation of oleoresin synthesis in living wood cells in U.S.A. southern and northern conifer species, such as slash, longleaf, and red pine, by treatment with 2-chloroethylphosphonic acid. This invention increases the amount of volatile and nonvolatile oleoresin extractives normally obtainable from the above-mentioned wood species. The increased oleoresins material can be recovered by normal extraction methods or as tall oil in conventional pulping procedures. The recoverable material consists of turpentine, rosin, and fatty acids normally considered generically as naval stores products.

2. Description of the Prior Art:

The prior art believed most relevant to this improvement is as follows:

(1) U.S. Pat. No. 3,839,823 assigned to the Secretary of Agriculture, U.S.A.

(2) U.S. Pat. No. 3,991,515 assigned to John Drew, SCM Corporation, New York, N.Y.

(3) Komissarov, D. A.; Frolov, Yu A., and Egorova, E.A., in Gidrolis Lesokkim Prom. 1968, 21(5), 21.

(4) Final office report of T. A. Harrington to the Naval Stores and Timber Production Laboratory of the U.S. Forest Service, Olustee, Fla., FS-SE 1501, Study NS 146, September, 1967.

(5) Final office report of Robert D. McReynolds of the Naval Stores and Timber Production Laboratory of the U.S. Forest Service, FS-SE 1502, Study NS 188, July 1975.

(6) The study plan of D. R. Roberts to the Naval Stores Laboratory of the U.S. Forest Service, FS-SE 1501, Study NS 165, May 1969, and Research Note SE 191, dated April 1973, from the U.S. Forest Service at Olustee, Fla.

(7) Proceedings of the Annual Meeting of the Lightwood Research Coordinating Council 1975, 1976, 1977, Jacksonville, Fla., specifically.

(a) "Ethylene-Diquat Synergism," W. J. Peters and D. R. Roberts. Presented Jan. 18 and 19, 1977. Distributed October 1977.

(b) "Ethylene—Potential Alternative to the Bipyridilium Herbicides for Lightwood Induction," K. E. Wolter, presented Jan. 18 and 19, 1977. Distributed October 1977.

The most pertinent parts of these references deal with the use of bipyridium herbicides paraquat and diquat (also known by the tradenames Gramoxone and Reglone, respectively; marks of the Imperial Chemicals Industries, Ltd.) and the use of primary amines. Paraquat and diquat, and primary amines, are applied systemically in sublethal doses into the xylem system of the tree. As a result, after a given period of time, oleoresin is synthesized in the living-wood cells and deposited in the tracheids of the xylem. This phenomenon is commonly known as "lightering," and the type of resinous wood produced is known as "lightwood."

The salient advantage of the present improvement, namely the use of ethylene of ethylene-releasing compounds, is its reduced toxicity to the person treating the tree as compared with the bipyridilium salts, paraquat and diquat, and the primary amine n-propylamine, whose effect is described in prior art reference 2 above. The $LD_{50}$ dosage (dosage at which 50 pct of the animals to whom the chemical was administered died) for 2-chloroethylphosphonic acid with rats is 4,229 mg/kg. The significantly reduced toxicity of 2-chloroethylphosphonic acid is apparent when compared with the $LD_{50}$ rate for n-propylamine and the bipyridilium salts, paraquat and diquat. The $LD_{50}$ dosage for n-propylamine with rats is 560 mg/kg. The $LD_{50}$ dosage for the bipyridilium salts, paraquat and diquat, with rats is 100 mg/kg. The OSHA standard for bipyridilium salts administered to humans is 0.5 $mg/m^3$. Gaseous ethylene released from 2-chloroethylphosphonic acid is toxic to mice at 950,000 ppm. In essence, ethylene gas excludes oxygen such that asphyxiation rather than the effects of ethylene gas alone is the cause of toxicity.

In addition, it is believed by the inventors that ethylene, a natural growth or senescence factor in plants, is directly responsible for the initiation of oleoresin synthesis. The aforementioned stimuli, such as the bipyridilium salts of primary amines, are throught to act physiologically by inducing a wounding or slow necrosis of living cells, which in turn initiate the endogenous production of ethylene, by the remaining living cells (consisting of ray parenchyma, epithelium and axial parenchyma cells), and subsequently stimulate the synthesis of oleoresins, a typical wounding response found under natural conditions.

It is difficult, however, to conclusively prove that ethylene alone initiates the production of oleoresin at the cellular level because any experimental manipulations of living trees or their constituent cells necessitates some sort of stress or wounding, which ultimately results in the natural production of oleoresins.

In normal stands, most Pinus species produce oleoresins as a result of natural stress, moisture stress, insects, and wind induced mechanical stress, such as torque, vibration, and bending. These stresses and the existence of resin canals account for the normal 3-4 percent of oleoresins found in pine wood on an extracted dry weight basis. Stimulation of this natural phenomenon by inflicting a series of wounds through tapping is the typical method for collection of oleoresins. This method restricts oleoresin production to the area of wounding. Alternatively, as in lightwood production, if a wounding stimuli is pervaded throughout the whole bole (and not localized at the wound face), all the affected living cells respond by increasing the synthesis of oleoresins. Paraquat and diquat treatments produce this response. Experimental data on systemically applied paraquat show a marked stimulation of endogenous ethylene production as well as a rapid increase in respiration rates, typical of cell stress or wounding responses. ("Proceedings of the Annual Meeting of the Lightwood Research Coordinating Council," January 18 and 19, 1977. Jacksonville, Fla., specifically, "Ethylene—Potential Alternative to the Bipyridilium Herbicides for Lightwood Induction," K. E. Wolter, published October 1977).

In addition to the bipyridilium herbicides, paraquat and diquat, the herbicide endothall (7-oxabicyclo (2.2.1) heptane-2, 3-dicarboxylic acid) is known to be an effective promoter of endogenous ethylene production in living plant cells. A salt of endothall, sold under the trademark Ripenthal, was very effective in inducing lightwood in 5-year-old red pine. Nonvolatile oleoresin extractives were increased to an average of 26.6 percent as compared with nontreated controls which contained an average of 3.3 percent oleoresins on an extracted dry weight basis. Ripenthal was only effective in younger tress. In more mature trees, Ripenthal migrated rapidly to the upper crown and needles, precluding increased production of oleoresins in the tree bole.

Use of a systemic application of an innocuous formulation of an ethylene-releasing compound such as 2-chloroethylphosphonic acid results in the living tree tissue responding in a similar fashion. However, in this case, it is solely the hormone ethylene that triggers synthesis of oleoresins in the pine bole. Therefore, the improvement not only involves a less toxic stimuli, but apparently mimics the normal and natural trigger mechanism for oleoresesin synthesis within cells; certainly a much more desirable procedure.

SUMMARY OF THE INVENTION

The invention discloses an improvement in the process of chemically stimulating the production of oleoresins in living cells of certain condiferous species by using stimuli of reduced toxicity to the user to duplicate stimuli of normal endogenous oleoresin production.

Such treatment comprises applying ethylene-releasing compounds systemically to xylem portions of the tree in either aqueous solutions or a gel. Application can be made at any given height and around the circumferences as long as the application procedure does not girdle the tree. Solutions of ethylene-releasing chemicals can be applied via shallow cuts made with a chisel, or in waterproof cups held close to a cut on the tree and holding a given amount and concentration of solution. An alternate method of aqueous application is via inclined bore holes into which the treating solution is dispersed. Nonaqueous solutions of ethylene-releasing chemicals can be applied in differing concentrations on a percent-by-weight basis either by application with a brush or as a bead of gel. Experience has shown that application of aqueous solutions is preferable. Other methods of application, such as the use of a high pressure needle or tree injector, will no doubt prove to be as effective in th application of aqueous treatment solutions.

Specific commercially available chemical compounds which release ethylene and are useful for the instant purpose include:
 B-hydroxyethylhydrazine
 ethylhydrazine
 sym-diethylhydrazine
 unsym-bis-(2-hydroxyethyl) hydrazine
 aminomorpholine
 2-hydroxy-N-(2-hydroxyethyl) carbazinate
 2-(2-hydroxyethyl) semicarbazine
 ethylpropyl phosphonate
 monoethyl sulfate
 2-chloroethylphosphonic acid The ethylene-releasing compound 2-chloroethylphosphonic acid is stable at a pH below 3.5, a typical aqueous solution of 2-chloroethylphosphonic acid having a pH of 1.0. After uptake of the treatment solution into the xylem transport system of the tree, which is normally above pH 5, the ethylene-releasing compound begins hydrolysis and releases ethylene into the xylem sap.

Trees suitable for use in this invention include:

| | | |
|---|---|---|
| Pinus banksiana | Pinus insularis | Pinus ponderosa |
| Pinus caribaea | Pinus jeffreyi | Pinus radiata |
| Pinus chihauhuana | Pinus khasya | Pinus resinosa |
| Pinus clausa | Pinus lambertiana | Pinus rigida |
| Pinus contorta | Pinus merkusii | Pinus serotina |
| Pinus echinata | Pinus monticola | Pinus sylvestris |
| Pinus elliottii | Pinus nigra | Pinus taeda |
| Pinus excelsa | Pinus palustris | Pinus teocote |
| Pinus glabra | Pinus patula | Pinus virginiana |
| Pinus gerardiana | Pinus pinaster | |

Ethylene-releasing chemicals applied in combination with the bipyridilium salts help spread their lightwood inducing effect over a greater portion of the treated trees and increases the extent of lightwood formation over what is obtained through the application of the bipyridilium salts alone.

The preferred mixture of the bipyridilium salts and ethylene-releasing compound contains 0.5 to 2.0%, by weight, bipyridilium salts, and ethylene-releasing chemical, here 2-chloroethylphosphonic acid, of 1 to 5% by weight. The effective amounts to chemically induce deposition of increased quantities of naval stores products within the living pine trees will be broader in range. Other ethylene releasing chemicals can be used. The amounts of bipyridilium salts and ethylene-releasing chemicals required for ideal stimulation of oleoresin production will vary with a tree's size for a given species.

An object of this invention is to provide an improved method of inducing lightwood formation in living pine trees. Another object of the invention is a method by which large quantities of naval stores products are deposited in the sapwood of growing pine trees. Still another object of this invention is the provision of a less toxic, more natural treatment that induces lightwood formation in a safer manner than any previously known method. A final object of the invention is the provision of a method that will increase the production and provide a stable supply of our naval status natural resources which are increasingly becoming scarce, valuable products.

DESCRIPTION OF THE PREFERRED EMBODIMENTS

In further illustration of this invention, the following examples and information are given. The improvement should not be limited to the ethylene-releasing compounds used, the methods of application, the time of application, the duration of the treatment, and the specific species used as test material.

EXAMPLE I

Replicate 20-year-old plantation-grown red pine (Pinus resinosa) of a given diameter class were coned with a watertight cup. Three-hundred milliliters of 2-chloroethylphosphonic acid in various concentrations were placed in the cups, and shallow cuts one-third the circumference were made with a chisel into the xylem portion of the bole under the solution, at approximately 1.5 meters above the ground level. The treatment solution was normally adsorbed within a 24-hour period; this depended, however, on climatic conditions such as temperature and relative humidity. Trees were sacrificed 6 months after treatment and analyzed for nonvolatile extractives at given distances from the point of application, over the entire cross-section of the tree, except where noted (Table I).

Doubling of the extractive content was obtained by treatment with 1.064 percent (wt.) 2-chloroethylphosphonic acid, as compared with water-treated controls. Additional portions of the cross section which showed visible lightering were also analyzed. In these portions, the increase in extractives was three to six times that of control trees. Also noted was an increase in dry weight percentage (oven dry weight/fresh weight) in 2-chloroethylphosphonic acid-treated trees, indicating that the treatment had dehydrated the trees. Similar dehydration occurs in paraquat-treated trees.

Table I

Percentages of nonvolatile extractives and dry weights of 2-chloroethylphosphonic acid-treated red pine trees and water-treated control trees

| Treatment | Distance[b] cm | Dry weight[c] Pct | Extractives[d] Pct |
|---|---|---|---|
| 2-chloroethyl-phosphonic acid:[e] | | | |
| 0.0213 | −15 | 43.1 | 3.1 |
| | +15 | 44.5 | 3.7 |
| | +50 | 46.6 | 3.4 |
| 0.213 | −15 | 45.5 | 3.4 |
| | +15 | 44.8 | 3.2 |
| | += | 46.5 | 3.4 |
| 1.064 | −15 | 54.1 | 4.0 |
| | 30− | 58.9 | 6.2(9.3)[f] |
| | +50 | 56.7 | 7.2(18.8)[f] |
| | +110 | 50.3 | 3.4 |
| | +150 | 50.1 | 3.8 |
| 2.127 | −15 | 66.5 | 5.4 |
| | +15 | 67.8 | 3.1 |
| | +50 | 69.7 | 3.1 |
| Control[g] (H$_2$O) | −15 | 55.3 | 3.3 |
| | +15 | 52.6 | 3.2 |
| | +50 | 44.3 | 3.3 |

[a] Trees treated 5/26/76 and harvested 11/2/76. Each tree received 300 milliliters of the indicated concentration of 2-chloroethylphosphonic acid.
[b] Distance in cm from point of treatment application.
[c] Ovendry weight/fresh weight.
[d] Percentage nonvolatile extractives based on the extracted dry weight of a sample of the entire cross section.
[e] Weight percentage 2-chloroethylphosphonic acid in 300 milliliters of the aqueous treatment solution.
[f] Percentage nonvolatile extractives isolated from the visible lightwood portion of each cross section based on the extracted dry weight basis of the visible lightwood portion of each cross section.
[g] Control trees were wounded and treated with water in the same manner as the 2-chloroethylphosphonic acid-treated trees.

EXAMPLE II

Replicate 40-year-old-slash pine (*Pinus elliottii* Engelm. var. *elliottii*) were treated with 5-milliliter aliquotes of 5 percent 2-chloroethylphosphonic acid in bore holes 0.6 meter above the ground. The trees were harvested in March, 1976, 2½ years after treatment. Analysis of total extractives was made for given portions of the bole beginning 0.5 meter below the point of treatment application (Table II).

Most of the increase in oleoresin production due to 2-chloroethylphosphonic acid treatment was located 0-3 meters from the point of treatment application. A greater increase in the volatile (turpentine) than in the nonvolatile (resin) oleoresins was noted in the treated trees. No visible lightwood was observed in the treated trees.

Table II

Percent oleoresin[a] in slash pine 2½ years after treatment with 5 percent (wt.) 2-chloroethylphosphonic acid

| Treatment | Distance from point of treatment application (meters) | | | |
|---|---|---|---|---|
| | 0-3 | 3-6 | Above 6 | Average |
| Control (H$_2$O)[b] | 2.3 | 3.7 | 2.8 | 2.9 |
| 5% (wt) 2-chloro ethylphosphonic acid | 4.3 | 3.7 | 3.1 | 3.6 |

[a] Percentage based on the dry weight of that section of the tree.
[b] Control trees were wounded and treated with water.

EXAMPLE III

A 10 percent (wt.) 2-chloroethylphosphonic acid gel, sold under the trademark Ethephon, was applied to new bark wounds of 100 slash pine (*Pinus elliottii* Engelm. var. *elliottii*) and 100 longleaf pine (*P. palustris*) every 2 weeks between March and October of 1973. At the end of this period, the trees were cut and the wood examined. Visible lightwood in both longleaf and slash pine existed in an irregular pattern throughout the sapwood. The lightwood was most heavily concentrated in the vicinity of the treatment application area on the bole and the visible lightwood extended 1 meter or more above the wound. These trees were not analyzed for extractives.

EXAMPLE IV

On Sept. 14, 1973, replicate slash pine (*Pinus elliottii* Engelm. var. elliottii) were treated with 5 milliliters of either 1 percent (wt.) paraquat, 1 percent (wt.) diquat, 1 percent (wt.) diquat plus 5 percent (wt.) 2-chloroethylphosphonic acid or 5 percent (wt.) 2-chloroethylphosphonic acid solutions placed in a bore hole. Each type of treatment was applied to 25 trees selected at random. One tree from each treatment was cut in January 1974. It was observed that the diquat plus 2-chloroethylphosphonic acid-treated tree had the greatest amount of visible lightwood. Six trees from each treatment were cut in March of 1974, approximately 6 months after treatment. The height of oleoresin soaked wood (visible lightwood) in paraquat-treated trees was less than in diquat-treated trees, which was less than diquat plus 2-chloroethylphosphonic acid-treated trees. 2-chloroethylphosphonic acid treatment alone, did not stimulate visible lightwood formation. Thus, during this 6-month treatment period, the diquat plus 2-chloroethylphosphonic acid-treatments increased resin yields at a greater height in the tree than did diquat, paraquat, or 2-chloroethylphosphonic acid treatments alone (Table III).

Table III

Rosin yields from slash pines 6 months after treatment with 2-chloroethylphosphonic acid, paraquat, diquat, and diquat plus 2-chloroethylphosphonic acid

| Distance above wound (meters) | Treatment | | | |
|---|---|---|---|---|
| | 2-chloroethyl-phosphonic acid | Paraquat | Diquat | Diquat +2-chloroethyl-phosphonic acid |
| | Pct Rosin[a] | | | |
| 3 | | | | 2.3 |
| 2 | | | | 2.7 |
| 1 | | | 2.3 | 2.9 |
| 0.5 | | 2.0 | 2.1 | 3.9 |

Table III-continued

Rosin yields from slash pines 6 months after treatment with 2-chloroethylphosphonic acid, paraquat, diquat, and diquat plus 2-chloroethylphosphonic acid

| Distance above wound (meters) | Treatment | | | |
|---|---|---|---|---|
| | 2-chloroethyl-phosphonic acid | Paraquat | Diquat | Diquat +2-chloroethyl-phosphonic acid |
| | Pct Rosin[a] | | | |
| 0 | 2.6 | 8.1 | 5.5 | 5.0 |

[a] Percent based on the extracted dry weight of the tree sample.

The same general pattern of yields was observed in trees cut 26 months after treatment, although 2-chloroethylphosphonic acid-treated trees were not examined. Visible lightwood heights in diquat plus 2-chloroethylphosphonic acid-treated trees extended higher than in diquat or paraquat-treated trees (Table IV). In the diquat plus 2-chloroethylphosphonic acid-treated trees at a height of 6.5 meters (21.5 ft) above the point of treatment the greatest oleoresin content was observed. Oleoresin content and visible lightwood were in very close correlation for trees treated with diquat, paraquat, or diquat plus 2-chloroethylphosphonic acid. Visible lightwood seldom extended beyond 2 meters (6.6 ft) in trees treated with paraquat, 2.5-3 meters (8.2-9.8 ft) in trees treated with diquat, and 4.5-5 meters (14.8-16.4 ft) in trees treated with a combination of diquat and 2-chloroethylphosphonic acid.

Table IV

Oleoresin content in the first 6.5 meters (21.5 ft) of slash pines 26 months after treatment

| Treatment | Distance above wound (meters) | | | | | | |
|---|---|---|---|---|---|---|---|
| | 0.05 | 0.5–1 | 1–1.5 | 1.5–2.5 | 2.5–4.5 | 4.5–6.5 | Average[b] |
| | Percent oleoresin[a] | | | | | | |
| Control[c] | 2.3 | 2.0 | 2.2 | 2.2 | 2.1 | 2.1 | 2.2 |
| 1% (wt) paraquat | 10.7 | 12.2 | 5.9 | 3.7 | 2.4 | 2.0 | 4.6 |
| 1% (wt) diquat | 8.9 | 9.6 | 4.5 | 3.5 | 2.8 | 1.9 | 4.1 |
| 1% (wt) diquat +5% (wt) 2-chloroethylphosphonic-acid | 9.8 | 11.2 | 7.7 | 5.8 | 4.5 | 3.7 | 6.0 |
| | — | — | — | — | — | — | — |

[a] Percent based on the extracted dry weight of that section of the tree
[b] Average per unit total volume.
[c] Untreated control slash pines.

EXAMPLE V

On October 6 and 7, 1975, a study was begun using replicate slash pine (*Pinus elliottii* Engelm. var. *elliottii*) to explore the action of 2-chloroethylphosphonic acid in combination with diquat and/or paraquat. Each tree in the study was treated three times. The first treatment was in October in 1975, the second in March of 1976, and the third in September of 1976. Each time 5 milliliters of a solution of 2-chloroethylphosphonic acid plus paraquat and/or diquat were applied to the tree in a bore hole angled to intersect approximately one-sixth of the trunk. After treatment, the bore hole was stoppered to prevent the escape of ethylene. The trees were cut during November and December of 1976. The results of this study demonstrate that ethylene from 2chloroethylphosphonic acid increases the lightwood stimulating effects of diquat and paraquat. Visible lightwood is observed at a greater height in the trees (Table V), and the amount of extractives obtained from the treated trees is increased (Table VI).

Table V

Average light wood heights observed in slash pines treated with different combinations of diquat, paraquat, and 2-chloroethylphosphonic acid

| Concentration of diquat or paraquat | Concentrations of 2-chloroethylphosphonic acid | | |
|---|---|---|---|
| | 0% | 1% (wt) | 5% (wt) |
| | Lightwood height (meters)[a] | | |
| 0.5% (wt) diquat CD) | 1.8 | 2.8 | 4.5 |
| .5% (wt) paraquat (P) | 1.4 | 2.0 | 2.8 |
| .25% (wt) D + .25% P | 1.5 | 2.3 | 3.7 |
| 2% (wt) diquat | 3.1 | 4.4 | 5.4 |
| 2% (wt) paraquat | 2.8 | 3.2 | 4.7 |
| 1% (wt) D + 1% P | 3.6 | 3.8 | 4.6 |

[a] Measured from point of treatment application.

Table VI

Extractive content[a] in the total merchantable length of slash pines 1.6 years after treatment

| Bipyridilium concentration | 2-Chloroethylphosphonic acid concentration | | | |
|---|---|---|---|---|
| | 0% | | 5% (wt) | |
| | 0.5% (wt) | 2% (wt) | 0.5% (wt) | 2% (wt) |
| Diquat | 15.2 | 17.3 | 17.5 | 21.6 |
| Paraquat | 14.8 | 17.1 | 17.3 | 20.9 |
| Diquat + paraquat[b] | 15.6 | 17.7 | 16.9 | 21.0 |

[a] Expressed as lbs. extractives per average tree.
[b] 0.5% (wt) = 0.25% (wt) diquat + 0.25% (wt) paraquat. 2% (wt) = 1% (wt) diquat + 1% (wt) paraquat.

The results indicate that there is no difference in action between the different bipyridiliums used. An increase in bipyridiliums concentration results in a higher extractive yield. The addition of 2-chloroethylphosphonic acid results in still higher extractive yields. The increase in extractive yield obtained with treatments of 2 percent (wt) bipyridilium and 0.5 (wt) percent 2-chloroethylphosphonic acid, are in every case (diquat, paraquat, diquat+paraquat), significantly higher than the increases observed with treatments of 0.5 percent (wt) bipyridilium and 0-5 percent (wt) 2-chloroethylphosphonic acid. If the oleoresin production effects of bipyridilium and 2-chloroethylphosphonic acid were merely additive, the increase in the amount of extractives produced by adding a given amount of 2-chloroethylphosphonic acid to a treatment solution containing any concentration of bipyridilium would be a constant. Our results show that the amount of increase in extractives produced is not a contant, but increases with an increase in the concentration of bipyridilium. Thus, we have shown that there is an interaction between bipyridilium and 2-chloroethylphosphonic acid which produces a more-than-additive increase in extractive yield when the two chemicals are combined.

Having thus disclosed our invention, we claim:

1. A method of chemically inducing the deposition of increased quantities of naval stores products within living pine trees by stimulating lightwood formation in large areas of said pine trees with an effective amount of a mixture of a bipyridilium salt and an ethylene releasing chemical; permitting the so-treated pine trees to grow for a time sufficient for lightwood development; harvesting the resulting pine trees; and extracting naval stores from the harvested tree.

2. The method of claim 1 wherein said bipyridilium salt is selected from the group consisting of paraquat and diquat and mixtures of same.

3. The method of claim 1 wherein the ethylene-releasing chemical is selected from the group consisting of B-hydroxyethylhydrazine, ethylhydrazine, sym-diethylhydrazine, unsym-bis-(2-hydroxyethyl) hydrazine, aminomorpholine, 2-hydroxy-N-(2-hydroxyethyl)carbazinate, 2-(2-hydroxyethyl semicarbazine, ethylpropyl phosphonate, monoethyl sulfate, and 2-chlorethylphosphonic acid.

4. The method of claim 2 wherein the bipyridilium salt is presented in a concentration of from 0.5 to 2% by weight.

5. The method of claim 3 wherein the ethylene-releasing chemical is 2-chloroethylphosphonic acid and is present in a concentration of from 1 to 5% by weight.

* * * * *